United States Patent
Müller et al.

[11] Patent Number: 5,509,297
[45] Date of Patent: Apr. 23, 1996

[54] VISCOMETER CALIBRATION

[75] Inventors: Gregory C. Müller; Theodore W. Selby, both of Midland, Mich.

[73] Assignee: Tannas Co., Midland, Mich.

[21] Appl. No.: 392,549

[22] Filed: Feb. 17, 1995

[51] Int. Cl.$^6$ .............. G01N 11/14; G01N 3/62; G01D 18/00

[52] U.S. Cl. .............. 73/54.32; 73/1 R; 73/54.17; 73/54.23

[58] Field of Search .............. 73/54.32, 1 R, 73/54.17, 54.19, 54.23

[56] References Cited

U.S. PATENT DOCUMENTS

| | | | |
|---|---|---|---|
| 3,875,791 | 4/1975 | Fitzgerald et al. | 73/59 |
| 4,299,119 | 11/1981 | Fitzgerald et al. | 73/59 |
| 4,571,989 | 2/1986 | Dealy | 73/60 |
| 4,899,576 | 2/1990 | November et al. | 73/59 |
| 5,012,667 | 5/1991 | Kruse | 73/1 R |
| 5,435,171 | 7/1995 | Chino et al. | 73/64.56 |

FOREIGN PATENT DOCUMENTS

| | | | |
|---|---|---|---|
| 266406 | 3/1990 | Japan | 73/1 R |
| 6323981 | 11/1994 | Japan | 73/1 R |
| 1157406 | 5/1985 | U.S.S.R. | 73/1 R |
| 1441267 | 11/1988 | U.S.S.R. | 73/1 R |
| 9004161 | 4/1990 | WIPO | 73/1 R |

*Primary Examiner*—Hezron E. Williams
*Assistant Examiner*—J. David Wiggins
*Attorney, Agent, or Firm*—Christopher John Rudy

[57] ABSTRACT

A rotational viscometer instrument of the type having a rotor driven to rotate about an axis, the rotor for contact with a fluid, the viscosity or related property of which can be measured by measuring torque or drag on the rotor rotating in contact with the fluid through a torque or drag measuring element, is improved by a means for interjecting a predetermined calibration factor into the instrument based on a viscosity of a fluid of known viscosity and the rotor and the torque or drag measuring element such that the true viscosity sensing ability of the instrument is enhanced.

9 Claims, 1 Drawing Sheet

VISCOMETER CALIBRATION

FIELD

The present invention concerns instrumentation and methodology useful in rotational viscometer calibration for testing of fluid viscosities.

BACKGROUND

The rotational viscometer or rheometer which has a digital readout capability such as among those of the well known LV series (Models LVDV-I+, LVDV-II+ and LVDV-III+) and RV series (Models RVDV-I+, RVDV-II+ and RVDV-III+) available from Brookfield Engineering Laboratories, Inc. (Stoughton, Mass.) and the well known Tannas Basic Rotary (TBR) (Trademarks of the Tannas Co., Midland, Mich.) viscometer available from the Tannas Co. (Midland, Mich.) in general measures torque or drag experienced by a rotating rotor because of the viscosity of a test liquid at low shear through deflection of a sensitive spring. This deflection is converted into appropriate electronic signals which may be displayed as a torque value and/or converted into and displayed as viscosity and/or other relevant values.

As with most instruments, these require calibration.

The longstanding practice in the art for calibration of such an instrument involves the use of calibration fluid(s) of known viscosity. In such calibration, a plot of known viscosity versus measured torque over the range of expected viscosity of the test sample at a specified rotor speed is often employed to convert the measured torque into the true viscosity. Also, for varying test samples, the longstanding practice associated with this in the field of rotational viscometry is to use one of a number of rotating spindles of various sizes depending upon the expected viscosity range of the test sample. In instruments such as these with digital readout capability, the spindle size is displayed and taken into account in calculating for the viscosity or related property displayed.

Accordingly, the following equation has been applied to determine viscosity in such instrumentation and methodology:

$$V = KST/\text{rpm} \quad (B)$$

wherein:

"V" is the viscosity in units of poise;
"K" is a torque constant related to the spring employed;
"S" is a spindle multiplier constant related to the particularly sized spindle employed;
"T" is the torque measured, and
"rpm" is the rotations per minute of the spindle.

Unfortunately, the foregoing method and instrumentation may lack the highest of accuracy. However, increasingly higher accuracy is demanded of viscosity testing, most especially in the low viscosity ranges. Moreover, the cost of instrumentation and the time required for operators to calibrate the instrument and to test fluids with it are of notable concern.

What is lacking and needed in the art is an instrument and method to ameliorate or overcome such problems, thus providing for increased accuracy at reasonable cost, and providing for simplified operation as well.

OTHER APPROACHES

For an extended time, such problems have been studied and attempted to be overcome. Numerous approaches have been tried, some of which provided little, if any, success. These include the following other approaches with respect to the aforementioned instruments and methods therewith:

1) More accurate leveling of the instrument.
2) Various rotor-stator arrangements to include larger rotors and stators.
3) Raising and lowering of the rotor in the test fluid.
4) A solid rotor shaft arrangement, of adverse effect.
5) A truncated rotor, wherein two opposing, vertically oriented, parallel faces in an otherwise cylindrical rotor were provided, which helped somewhat at low end viscosity ranges.
6) A smaller rotor, which helped somewhat at high end viscosity ranges.

However, basic problems as aforementioned remained unsolved. Indeed, it is a great illusion that things are as simple as they seem with respect to the viscosity testing art.

OBJECTS

It is an object of the present invention to ameliorate or overcome such problems in the art as aforesaid.

It is an object hereof to provide a new, improved viscometer instrument and method capable of measuring at low shear rates and stresses the true viscosity of a fluid with better accuracy than heretofore known.

It is a further object hereof to provide effective calibration of the instrument to +0.01/−0.01 centipoise (cP) at low viscosity, e.g., about 20 cP or lower, to a 0.1 cP change at somewhat higher viscosity, e.g., about 100 cP, and generally to about 0.1 percent (%) at all viscosities.

It is an object hereof to provide such an instrument which is cost effective and simple to operate.

It is a further object hereof to provide such an instrument and method with the capability to internally evaluate and set an appropriate calibration to display the corresponding viscosity for increased operator knowledge and efficiency.

Additional objects of the invention are apparent from a reading of the specification hereof, to include as follows.

SUMMARY

After a long period of dedicated research, from which, among other significant things, the source of the problem was finally recognized, the present invention was developed. It provides, in general, in a rotational viscometer instrument having a rotor driven to rotate about an axis, the rotor for contact with a fluid, the viscosity or related property of which can be measured by measuring torque or drag on the rotor rotating in contact with the fluid through a torque or drag measuring element, the improvement which comprises a means for interjecting a predetermined calibration factor into the instrument based on a viscosity of a fluid of known viscosity and the rotor and the torque or drag measuring element such that the true viscosity sensing ability of the instrument is enhanced.

The invention is useful in measuring fluid viscosity.

Significantly, in satisfaction of all or a part of its objects, whereas heretofore other approaches to include the frequent changing of spindles and the entering of a factor into the instrument based on spindle geometry attempted to correct for viscosity readout, and contrary to additional approaches taken such as aforesaid which even experts in the art would propose as effective, the invention fundamentally differs from these approaches in that it goes to the innate viscosity sensing ability in the instrument for any type of equipment to include the spindle or rotor employed. Thus, it results in significantly higher accuracy. Calibration is highly simplified in that only one Newtonian reference fluid is required. The invention is readily manufactured and significantly simple in operation, and it is cost effective.

Numerous further advantages attend the invention.

DRAWINGS

The drawings form part of the specification hereof. In the drawings, the following is briefly noted:

ILLUSTRATIVE DETAIL

Herein, in general, the term "viscometer" includes both viscometer and rheometer instrumentation and methodology, unless otherwise specified or manifest from the context.

It has been discovered that the following equation applies:

$$V = KSCT/rpm + C'$$

wherein:

"V" is the viscosity in units of poise;

"K" is a torque constant related to the spring employed;

"S" is a spindle multiplier constant related to the particularly sized spindle (rotor) employed;

"C" is a calibration constant related to the incremental change necessary to align the viscometer readout to the true viscosity;

"T" is the torque measured;

"rpm" is the rotations per minute of the spindle, and

"C'" is another calibration constant related to the internal friction of the instrument.

(Of course, to obtain the viscosity in units of centipoise, one need merely multiply KSCT/rpm by a factor of 100 units.) Solving for "C" there is obtained the following equation:

$$C = (V(rpm)/KST) - C' \qquad (II)$$

and with "C'" presumed negligible, as especially relevant to viscosity measurements done following calibration to a known standard and also to higher viscosity values, there is obtained the following equation:

$$C = V(rpm)/KST \qquad (III)$$

wherein the entries for equations I, II & III are the same.

Figure 1:
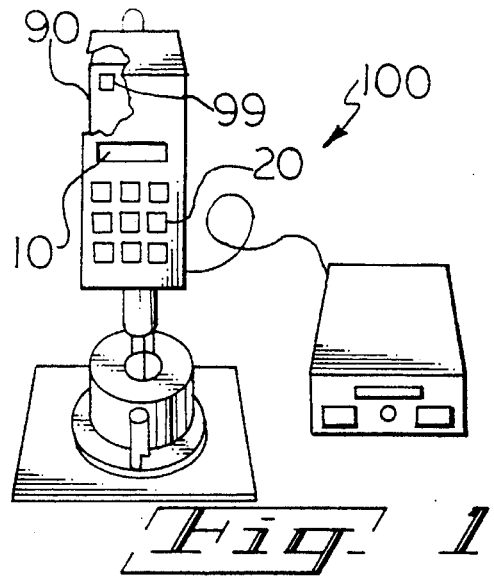
FIG. 1 is a general partial cut-away view of a low shear rate rotational viscometer of the present invention.

For example, a commercially available Tannas Basic Rotary low shear viscometer equipped with standard circuitry and electronics and a Brookfield LV torque measuring spring, as generally in the commercially available LVDV-II+ model Brookfield viscometer, is modified to provide new, improved, low shear rotary viscometer 100 (FIG. 1). In such equations as I, II &III above, a desirable entry value of "C" becomes 2.310 units, with "V" at 0.1236 P (12.36 cP) as for a standard reference Newtonian test liquid, "T" at 68.5 units, "K" at 0.9373 units, "S" at 10.0 units, and "rpm" at one hundred twenty rotations per minute. This can be entered into the instrument in any of a number of ways, as those skilled in the art would appreciate.

Although readout needle or reading scale adjustments might be made such as by Bending, slipping, screwing, and so forth in manual rotational viscometers as means to interject the calibration factor, it is advantageous to interject the calibration factor into a rotational viscometer having an electronic sense processing unit. In electronics-containing rotational viscometers, the calibration factor may be interjected into suitable digital and/or analog processing circuitry, as appreciated by those skilled in the art.

Figure 2:
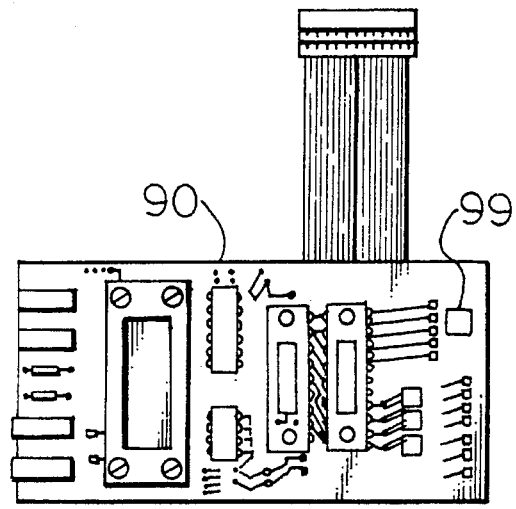
FIG. 2 is a view of a circuit board for installation of an integrated circuit chip employable with the invention.

Preferably, sequential values of "C" are programmed or blown into the processing program of a standard eight-prong integrated circuit chip 99 which is then inserted into the circuitry board 90 of the instrument as, for example, the commercially available circuit board number "DVB 13B" which may include diode circuitry suitable for AND/OR, NOR, AND/IF and so forth type logic, for example, in replacement of a corner chip with which the commercially available instrument would otherwise be equipped (FIGS. 1 & 2). This modifies the readout of viscosity or related property to approach more accurately and precisely its true value, and the value of "C" is predetermined according to the desired calibration increment. A related identity, for example, an alphanumeric identity, may be displayed on instrument display window 10. Accordingly, the following table obtains with the formula for modified TBR viscometer 100 having the LV type spring:

| Display Setting | Entry "C" |
| --- | --- |
| AA | 2.264 |
| AB | 2.270 |
| AC | 2.274 |
| AD | 2.278 |
| AE | 2.282 |
| AF | 2.286 |
| AG | 2.290 |
| AH | 2.294 |
| AI | 2.298 |
| AJ | 2.302 |
| AK | 2.306 |
| AL | 2.310 |
| AM | 2.314 |
| AN | 2.318 |
| AO | 2.322 |
| AP | 2.326 |
| AQ | 2.330 |
| AR | 2.334 |
| AS | 2.338 |
| AT | 2.342 |
| AU | 2.346 |
| AV | 2.350 |
| AW | 2.354 |
| AX | 2.360 |
| AY | 2.364 |
| AZ | 2.368 |

Figure 3:
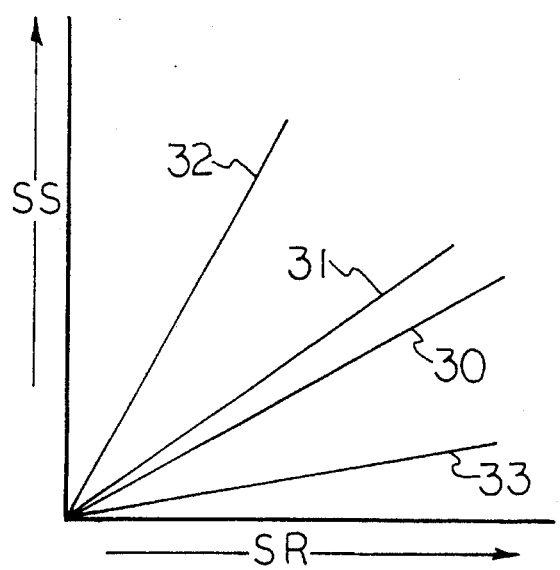
FIG. 3 is a graph of shear stress versus shear rate.

This generally corresponds to corrections of a suitable increment as on a twenty-four step correction graph (FIG. 3) where shear stress SS is plotted against shear rate SR. The function 30 indicates the true viscosity of a fluid, and the function 31 indicates measured viscosity of the fluid which approaches a first incremental correction factor such as is associated with a central value of entry constant "C" with display setting "AL" from the table above (a 0.004 unit incremental correction factor change) from which viscometer 100 can be set to output true viscosity value. Functions 32 & 33 represent outer bounds of the correction factor range.

Figure 4:
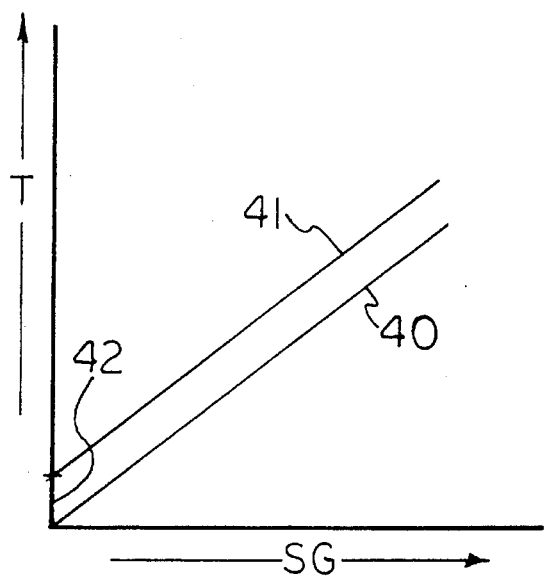
FIG. 4 is a graph of torque versus shear gradient.

As for the value of "C'" it too can be calculated for, as by employing comparison to standard liquids with known viscosity with the assistance of an additional correction graph (FIG. 4) where torque T is plotted against shear gradient SG. The function 40 indicates the true viscosity of a Newtonian fluid, and the function 41 indicates measured viscosity of the fluid. The slight displacement 42 from the origin found at the lower end of viscosity for the fluid is the result of internal instrumental friction, which can be determined by reiterative or estimative calculation with the following equation:

$$C'=V-KSCT \qquad (IV)$$

wherein the entries are the same as those for equation I.

The value for "C'" can also be interjected into the instrument in any of a number of ways, as suitably akin for "C" above, as those skilled in the art would appreciate. As well, the value of "C'" may be programmed into the standard chip 99 inserted into the circuitry 90 of the instrument 100 so as to modify the readout of viscosity or related property to approach more accurately and precisely its true value.

Thus, correction for the internal friction of the instrument can be calculated for as well. However, the correction for such friction is optional.

In order to operate viscometer 100, the operator need only test the instrument viscosity readout against one fluid reference standard of known viscosity, say, of 12.36 cP. As the instrument 100 displays a viscosity, say, 12.52 cP, the operator simply enters the appropriate correction factor as by the entry of a suitable number of values to incrementally change the calibration factor through the push of button 20 until the correct viscosity is displayed by the instrument. Preferably, window 10 displays the calibration factor as a display setting such as tabulated above. With instrument 100 thus calibrated, a test fluid or series of test fluids with a viscosity in the general range of the reference fluid can be measured for viscosity or related property.

Thus, the invention differs from any other method or instrument in viscosity testing known to date. Usually one calibrates a rotational viscometer with a set of Newtonian fluids, the fluids being set to modify the values from the viscometer as an interpretation of some function of viscosity. In the practice of the present invention, the viscometer is accurately matched to the fluid, and typical calibration can be effected with one suitable Newtonian reference fluid. It may be said that the invention changes the viscosity sensing ability of an instrument.

And so, the invention provides for significantly higher accuracy than heretofore available in low shear viscometers. In general, it provides for effective calibration of the low shear viscometer to about 0.1% at all suitable viscosities. More particularly, it provides for effective calibration of the low shear viscometer to +0.01/−0.01 cP at low viscosity, e.g., about 20 cP or lower, and to a 0.1 cP change at somewhat higher viscosity, e.g., about 100 cP.

Accordingly, the enhancement of the true viscosity sensing ability with the viscometer can be substantial.

In view of the foregoing, it can be seen that the instrument of the present invention can be considered to be calibrated by an improved means for yielding true viscosity measurements, having an electronic drive control module, output response readout module, and correction determination and calibration factor interjection module, and that the means for interjecting a predetermined calibration factor into the instrument can be considered to be included therewith and based on a multi-part system including a viscosity of a fluid of known viscosity and the rotor and the drag measuring element, such that the true viscosity sensing ability of the instrument is enhanced. It may be further considered that, thus, a logical means of interjecting a predetermined calibration factor into the instrument becomes apparent—by choosing a proper calibration factor for the known fluid viscosity by loading a proper constant from a stored table of calibration constants (in memory) into the correction interjection and feedback module.

CONCLUSION

The present invention is thus provided. Numerous modifications can be effected within its spirit, the literal claim scope of which is particularly pointed out as follows:

We claim:

1. In a rotational viscometer instrument having a rotor driven to rotate about an axis, the rotor for contact with a fluid, the viscosity or related property of which can be measured by measuring drag on the rotor rotating with the rotor in contact with the fluid through a drag measuring element, the improvement which comprises the instrument being calibrated by an improved means for yielding true viscosity measurements, having an electronic drive control module, output response readout module, and correction determination and calibration factor interjection module, to include by a means for interjecting a predetermined calibration factor into the instrument based on a multi-part system including a viscosity of a fluid of known viscosity and the rotor and the drag measuring element, such that the true viscosity sensing ability of the instrument is enhanced.

2. The instrument of claim 1, which has an electronic sense processing unit as part of said interjecting means.

3. The instrument of claim 2, wherein said interjecting means includes a programmed integrated circuit chip to automate the calibration process based on a known range of fluid viscosities for a reference fluid, and on rotor size.

4. The instrument of claim 1, wherein calibration is effective to an accuracy of about 0.1% at all suitable viscosities.

5. The instrument of claim 2, wherein calibration is effective to an accuracy of about 0.1% at all suitable viscosities.

6. The instrument of claim 3, wherein calibration is effective to an accuracy of about 0.1% at all suitable viscosities.

7. The instrument of claim 1, wherein internal friction is accounted for with the calibration factor.

8. The instrument of claim 2, wherein internal friction is accounted for with the calibration factor.

9. The instrument of claim 3, wherein internal friction is accounted for with the calibration factor.

* * * * *